United States Patent [19]

Raynolds et al.

[11] Patent Number: 5,800,990

[45] Date of Patent: Sep. 1, 1998

[54] ANGIOTENSIN-CONVERTING ENZYME GENETIC VARIANT SCREENS

[75] Inventors: Mary V. Raynolds, Englewood; M. Benjamin Perryman, Denver, both of Colo.

[73] Assignee: Regents of the University of Colorado, Boulder, Colo.

[21] Appl. No.: 568,271

[22] Filed: Dec. 6, 1995

[51] Int. Cl.$^6$ .............................. C12Q 1/68; C12P 19/34
[52] U.S. Cl. .................................................. 435/6; 435/91.2
[58] Field of Search ..................... 435/6, 91.1, 91.2; 536/24.3, 24.33

[56] References Cited

U.S. PATENT DOCUMENTS

| | | | |
|---|---|---|---|
| 5,359,045 | 10/1994 | Soubrier et al. | 536/23.2 |
| 5,480,793 | 1/1996 | Soubrier et al. | 435/212 |

OTHER PUBLICATIONS

Agerholm–Larsen et al. (Oct. 1995) Circulation (suppl I) vol. 92, p. I-800.
Ueda et al. (1996) J. Endocrinology, vol. 148 (suppl), abstract OC16.
Villard et al. (1996) Am. J. Hum. Genet. 58:1268–78.
Ludwig et al. (1995) Circulation 91:2120–2124.

*Primary Examiner*—W. Gary Jones
*Assistant Examiner*—Amy Atzel
*Attorney, Agent, or Firm*—Frederick W. Pepper

[57] ABSTRACT

Rapid screening methods are described for determining human patients at risk of developing cardiovascular disease. The screening involves, for example, comparing an angiotensin-converting enzyme genomic DNA of a patient with a sequence region of angiotensin-converting enzyme gene from a person with no mutations in the region. The invention features methods of analyzing the predisposition of patients to cardiovascular disease which involves detecting small deletions, insertions, and point mutations in the angiotensin-converting enzyme gene. Small deletions, insertions, or point mutations can be detected by detecting mismatches between an angiotensin-converting enzyme genomic DNA sequence or angiotensin-converting enzyme genomic DNA-polymerase chain reaction products from a patient and a probe specific for a sequence region of angiotensin-converting enzyme gene from a person with no mutations in the region.

8 Claims, 2 Drawing Sheets

Fig. 1

Fig. 2

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:1:

GCTGCCGCTG CTGTTGCTGC      20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:2:

AGGCCCCCGT GTCTGTGAAG      20

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:3:

CAACTGGACG CCGAACTC                                                                                      18

( 2 ) INFORMATION FOR SEQ ID NO:4:

( i ) SEQUENCE CHARACTERISTICS:
          ( A ) LENGTH: 18 base pairs
          ( B ) TYPE: nucleic acid
          ( C ) STRANDEDNESS: single
          ( D ) TOPOLOGY: linear       ( i i ) MOLECULE TYPE: cDNA       ( x i ) SEQUENCE DESCRIPTION: SEQ ID NO:4:

GGGCGATGCC CAGGAAGA                                                                                      18

( 2 ) INFORMATION FOR SEQ ID NO:5:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear       ( i i ) MOLECULE TYPE: DNA (genomic)

( x i ) SEQUENCE DESCRIPTION: SEQ ID NO:5:

AACGAGCTGC ATGGGGAGAA                                                                                    20

( 2 ) INFORMATION FOR SEQ ID NO:6:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear       ( i i ) MOLECULE TYPE: DNA (genomic)

( x i ) SEQUENCE DESCRIPTION: SEQ ID NO:6:

GTGGCTACCA GCAGGGCGAT                                                                                    20

( 2 ) INFORMATION FOR SEQ ID NO:7:

( i ) SEQUENCE CHARACTERISTICS:
          ( A ) LENGTH: 18 base pairs
          ( B ) TYPE: nucleic acid
          ( C ) STRANDEDNESS: single
          ( D ) TOPOLOGY: linear       ( i i ) MOLECULE TYPE: DNA (genomic)

( x i ) SEQUENCE DESCRIPTION: SEQ ID NO:7:

CAACTGGACG CCGAACTC                                                                                      18

( 2 ) INFORMATION FOR SEQ ID NO:8:

( i ) SEQUENCE CHARACTERISTICS:
          ( A ) LENGTH: 18 base pairs
          ( B ) TYPE: nucleic acid
          ( C ) STRANDEDNESS: single
          ( D ) TOPOLOGY: linear       ( i i ) MOLECULE TYPE: DNA (genomic)

( x i ) SEQUENCE DESCRIPTION: SEQ ID NO:8:

GGGCGATGCC CAGGAAGA                                                                                      18

ANGIOTENSIN-CONVERTING ENZYME GENETIC VARIANT SCREENS

FIELD OF THE INVENTION

The present invention relates to methods for determining mutations in the angiotensin-converting enzyme (ACE) gene of a patient. The determination of such mutations is used to predict the patient's actual risk for developing a specific cardiovascular disease.

BACKGROUND OF THE INVENTION

The renin-angiotensin system (RAS) is an endocrine cascade which traditionally has been thought to regulate blood volume, vascular tone, and Na homeostasis. Angiotensin-converting enzyme (ACE), the final enzyme in the cascade, is the key catalytic step in production of the peptide hormone angiotensin II (Ang II). The enzyme cleaves two amino acids from the inactive prohormone angiotensin I (Ang I) to form the biologically active octapeptide Ang II, a potent vasoconstrictor. In addition, ACE inactivates bradykinin (BK) in a two-step cleavage process first to the inactive peptide BK 1-7 followed by further cleavage to BK 1-5 (Stewart, *Handbook of Inflammation, Volume 6: Mediators of the Inflammatory Process*, pp. 189–217, Elsevier Science Publishers (1989)). ACE is also capable of hydrolyzing other peptides, including some neuropeptides such as gonadotropin-releasing hormone (Skigdel and Erdos, *J. Clin. and Exper. Theory and Practice* A9(2&3):243–259 (1987)).

ACE is a zinc metallopeptidase which is membrane bound. The enzyme is expressed most abundantly by endothelial cells, particularly in the pulmonary circulation. ACE is also found in absorptive epithelial cells, neuroepithelial cells, and male germinal cells (Wei et al., *J. Biol. Chem.* 266:9002–9008 (1991)). In addition, ACE is expressed in the heart, primarily by stromal cells (Schunkert et al., *Circulation* 87:1328–1339 (1993)), but also by cardiac myocytes (Sadoshima et al., *Cell* 75:977–984 (1993)).

ACE is a glycoprotein composed of a single peptide chain of approximately 170 kDa (Wei et al., *J. Biol. Chem.* 266:5540–5546 (1991)). The carboxy terminus of the protein has a short cytoplasmic tail and a 17 amino acid transmembrane domain which integrates the ACE into the cell membrane. Most of the protein consists of an extracellular domain (1230 amino acids) containing two predicted catalytic sites based on sequence homology with other metallopeptidases.

ACE is encoded by a single copy gene on human chromosome 17q23. The gene comprises 26 exons and 25 introns spanning 21,000 base pairs. The gene appears to have arisen by gene duplication as the two halves of the extracellular domain, containing the putative active sites, are highly homologous (Hubert et al., *J. Biol. Chem.* 266:15377–15383 (1991)).

Binding studies using competitive ACE inhibitors (Vago et al., *Br. J. Pharmacol.* 107:821–825 (1992)) and analysis of the zinc content (Wei et al., *J. Biol. Chem.* 266:9002–9008 (1991)) are consistent with only a single binding site on each ACE molecule. The two catalytic sites have been analyzed by deletions or point mutations in a cDNA expression construct. The analysis indicated that each site is enzymatically active and absolutely requires Zn. However, the binding sites require different chloride ion concentrations for catalytic activity. The amino terminal active site requires an order of magnitude less chloride ion than the carboxy terminal site. In addition, the two active sites appear to have different catalytic constants for Ang I cleavage (Wei et al., *J. Biol. Chem.* 266:9002–9008 (1991)). The amino terminal site is less active against Ang I than the carboxy terminal site. These data suggest that both catalytic sites are active, but may have different functions due to different requirements for the chloride ion. For example, BK hydrolysis is less chloride ion dependent than Ang I conversion. Therefore, one site may mediate BK cleavage and the other Ang I conversion. Both sites are in the extracellular domain.

The RAS has recently been implicated as an important adverse pathogenic mechanism in cardiovascular disease (Dzau, *Circulation* 77:4–13 (1988)). As stated above, ACE plays a key role in the RAS. The enzyme converts Ang I to Ang II and also hydrolyzes vasodilator and antiproliferative kinins such as BK. The Ang II produced by the action of ACE also has powerful non-vasoconstrictive effects. Ang II can promote proliferation of myocardial and vascular smooth muscle and cause neointimal hyperplasia after arterial wall injury (Lindpaintner et al., *J. Cardiovasc. Pharmacol.* 20:S41–S47 (1992)). Although Ang I can be converted to Ang II in the absence of ACE (Kinoshita et al., *J. Biol. Chem.* 266:19192–19197 (1991), Urata et al., *J. Clin. Invest.* 91:1269–1281 (1993), Urata et al., *Circ. Res.* 66:883–890 (1990)), administration of an ACE inhibitor substantially diminishes the proliferative and pressor effects of Ang I, suggesting that ACE-mediated production of Ang II is an important physiologic process (Swales and Dzau, *Am. Heart J.* 123:1412–1413 (1992)). The RAS has been implicated in cardiovascular disease primarily because of its role in fluid volume and blood pressure control, but the growth promoting effects of Ang II on smooth muscle and myocardium may also be directly involved in disease processes. In addition, increased ACE-mediated hydrolysis of BK, a potent local vasodilator, may have adverse effects. BK has antiproliferative effects on some cell types, including vascular smooth muscle cells (Farhy et al., *Circ. Res.* 72:1202–1210 (1993), Linz and Scholkens, *Eur. Heart J.* 14:81:Abs 605 (1993)). Thus, BK may modulate the mitogenic effects of Ang II.

The RAS has both a circulating endocrine or hormonal component, derived from the kidney and liver, respectively. It also has a locally derived paracrine or autocrine component, particularly in the vasculature and myocardium. There is abundant evidence for local production of all components of the RAS in several tissues, including kidney, brain, adrenal gland, blood vessels, and heart (Dzau, *Circulation* 77:4–13 (1988)). Although renin expression in the myocardium is controversial (von Lutterotti et al., *Circulation* 89:458–470 (1994)), the evidence for local production of ACE and angiotensin is more compelling (Dzau and Re, *Circulation* 89:493–498 (1994)). Renin and ACE enzyme activity have been detected in isolated perfused rat hearts (Cross et al., *Life Sci.* 29:903–908 (1981)). In addition, renin, angiotensinogen, the precursor of Ang I, and ACE mRNA species have been found by Northern blot analysis of RNA isolated from heart (Kunapuli and Kumar, *Circ. Res.* 60:786–790 (1987, Schunkert et al., *J. Clin. Invest.* 86:1913–1920 (1990)). Also, Ang II has been produced in isolated hearts perfused with angiotensin I (in the complete absence of serum). This suggests the presence of a tissue ACE in myocardium (Linz et al., *J. Cardiovasc. Pharmacol.* 8:S91 (1986)). The local tissue RAS appears to be more important than the circulating system for tonic maintenance of blood pressure and fluid volume. Both angiotensinogen and ACE expression is increased in the myocardium in animal and human heart failure without concomitant increases in other tissues such as lung or kidney. When ACE inhibitors are administered to hypertensives, blood pressure remains depressed long after circulating renin, angiotensin and ACE levels have returned to their pretreatment values (Dzau, Circulation 77:4–13 (1988)). ACE inhibitors also lower blood pressure in normotensive individuals with normal levels of circulating renin and ACE (Dzau, Circulation 77:4–13 (1988)).

The RAS has been implicated in left ventricular remodelling after myocardial infarction. This results in progressive left ventricular dilation and contractile dysfunction (J. Cardiovasc. Pharmacol. 20:S41–S47 (1992)). In an experimental animal model of heart failure, ACE activity and ACE mRNA expression were induced in the myocardium of rats after coronary artery ligation compared to control or sham operated animals. ACE expression was induced most in the right ventricle of rats with heart failure, but ACE was also expressed in the left ventricle and interventricular septum in these animals at higher levels than in control animals (Hirsch et al., Circ. Res. 69:475–482 (1991), Schunkert et al., Circulation 87:1328–1339 (1993)). As the expression of myocardial ACE is inducible, local ACE may be rate limiting for Ang II production.

Expression and activity of components of the RAS may be regulated by several mechanisms. First, expression of the local RAS in the myocardium may be regulated by hormonal or neuroendocrine signals (Orth et al., Textbook of Endocrinology, William Saunders Co., 506–507 (1992)) or by changes in load (Sadoshima et al., Cell 75:977–984 (1993)). Second, genetic variants in RAS components may alter activity of one member of the cascade, affecting local Ang II production.

Genetic variance in components of the RAS system may affect Ang I to Ang II conversion. This in turn may alter ventricular remodelling after an insult to the myocardium. ACE mRNA abundance and ACE activity are increased in experimental animal models of heart failure (Hirsch et al., Circ. Res. 69:475–482 (1991)) and in human heart failure (Studer et al., Circulation 86:I-119:abs 475 1993)). Furthermore, chronically increased ACE expression appears to be deleterious to the myocardium. This is indicated indirectly by the effects of ACE inhibitors on preventing progressive left ventricular dysfunction in animals and humans (Dzau and Hirsch, Euro. Heart J. 11:65–71 (1990), Pfeffer et al., N. Eng. J. Med. 327:669–677 (1992), N. Eng. J. Med. 325:293–302 (1991)). Recent data suggest that genetic variants in ACE may be very important in determining the effects of ACE in cardiovascular disease (Soubrier and Cambien, TCM 3:250–258 (1993)). Polymorphic markers in intron 16 of the ACE gene have been shown to be associated with risk for coronary artery disease (Cambien et al., Nature 359:641–644 (1992)) and with risk for developing end stage heart muscle disease (Marian et al., Lancet 342:1085(1993), Raynolds et al., Lancet 342:1073–1075 (1993)). The polymorphic markers consist of the presence (I) or absence (D) of a 287 base pair alu repeat sequence. Individuals homozygous for the I allele (I/I genotype) have the lowest circulating ACE levels (Tiret et al., Am J. Hum. Genet. 51:197–205 (1992)). Individuals carrying the I/D genotype have intermediate levels of ACE, whereas those homozygous for the D/D allele have the highest ACE levels (Tiret et al., Am J. Hum. Genet. 51:197–205 (1992)). Individuals homozygous for the D allele (D/D genotype) have an increased risk of developing cardiovascular disease. The polymorphism associated with intron 16 does not appear to be directly responsible for the variance in ACE levels or for the onset of heart disease, but is in strong linkage disequilibrium with the true variant or variants in the ACE gene locus.

SUMMARY OF THE INVENTION

This invention concerns a method of screening human patients to determine those at risk of developing cardiovascular disease. This screening involves, for example, comparing an angiotensin-converting enzyme genomic DNA of a patient with a sequence region of angiotensin-converting enzyme gene from a person with no mutations in the region. The invention features a method of analyzing the predisposition of patients to cardiovascular disease which involves detecting mutations or detecting the location of small deletions, insertions, and point mutations in the angiotensin-converting enzyme gene. A mutation or the location of small deletions, insertions, or point mutations can be detected by detecting mismatches between an angiotensin-converting enzyme genomic DNA sequence or angiotensin-converting enzyme genomic DNA-polymerase chain reaction (PCR) products from a patient and a detectable probe specific for a sequence region of angiotensin-converting enzyme gene from a person with no mutations in the region. One of the probes is prepared from a 287 base pair region of the angiotensin-converting enzyme gene which spans 134 base pairs of the 3' region of exon 25 and the 5' region of exon 26 and the entire 153 base pairs of intron 25.

DETAILED DESCRIPTION OF THE INVENTION

It has been determined that alternatively spliced ACE mRNA species are expressed in the intact left ventricle. The mRNA expressed by the heart (probably by cardiac myocytes as these represent 70–80% of the total cell mass in the myocardium) encodes a protein containing extra amino acids. Furthermore, mutations in intron 25 of the ACE gene have been identified in a region of the intron which is retained in the mature ACE mRNA in the heart. Thus, the mutations will alter the amino acid sequence of the enzyme, but only in the heart. These mutations include an A to G transition 6 nucleotides away from the 3' splice acceptor site in intron 25 and insertions in intron 25 near the splice acceptor site. Another mutation identified is a 5 base pair insertion immediately 3' of the splice acceptor site in exon 26. The mutations cluster in a region of the ACE protein which is proximal to a carboxypeptidase cleavage site. ACE is an integral membrane protein with a large extracellular domain containing two active sites. The release of ACE from the cell membrane is a regulated step (Ranchandran et al., J. Biol. Chem. 269:2125–2130 (1994) and is mediated by carboxypeptidase Y. Therefore, mutations clustering near the cleavage site may alter proteolytic removal if the enzyme from the cell membrane, with implications for local Ang II production.

Other regions in the mature ACE protein may contain mutations in addition to those found near the consensus cleavage site. Either of the active sites may contain loss or gain of function mutations, which will affect the conversion of Ang I to Ang II or will affect bradykinin hydrolysis.

The amino terminal active site spans the region between amino acids 360-370 (nucleotides 1187-1219). The carboxy terminal active site spans the region between amino acids 958-970 (nucleotides 2981-3019). Amino acid and nucleotide sequences are numbered according to the ACE sequence published by Soubrier et al., *Proc. Nat. Acad. Sci. USA* 8:9386-9390 (1988). It is the carboxy terminal active site which is the dominant site of Ang I conversion to Ang II. Induction of the cardiac-specific isoforms of ACE are very important in inducing pathogenic changes in the heart in the absence of increased ACE expression in other tissues.

The present invention relates to rapid screening methods for identifying individuals who are heterozygous or homozygous for the mutations, proximal to the regulated cleavage site, clustering in intron 25 of the ACE gene. This is the intron retained in the heart. Also the present invention can be used to detect mutations in the active site regions or in other as yet unidentified regions of the ACE cDNA. The screening methods use a labeled probe, complementary to a 287 base pair region of the ACE gene which spans 134 base pairs of the 3' region of exon 25 and the 5' region of exon 26 and the entire 153 base pairs of intron 25 (Hubert et al., *J. Biol. Chem.* 266:15377-15383 (1991)), to detect mismatches between the probe and sample DNA. A DNA fragment corresponding to this region is cloned. This cloned DNA fragment, used as a probe, is from ACE genomic DNA derived from an I/I individual. Subsequent cloning and sequencing of DNA fragments from the same region of the ACE gene in other I/I individuals showed that the sequence is conserved in the I/I genotype. This result confirms that this sequence region can serve as a probe to scan for mutant alleles. An antisense RNA probe labeled to allow detection, is transcribed from the cloned DNA fragment, the I/I construct from the ACE gene, which is in a transcription competent plasmid vector (pCRII, Invitrogen, San Diego, Calif.).

The labeled antisense RNA probe is hybridized in solution with ACE genomic DNA or PCR amplified ACE DNA from the above 287 base pair region for 12-18 hours. The RNA:DNA hybrids are digested with a mix of RNase A and RNase T1, which cleaves the hybrids in regions of mismatch. This digestion generates protected fragments smaller than the full length probe. For example, if the DNA sample contains a single base pair substitution that results in a mismatch recognized by the RNases, two new RNA fragments are detected. The total size of these fragments equals the size of the single fragment observed with DNA from an I/I individual. The RNA:DNA hybrids are resolved by denaturing gel electrophoresis and detected by autoradiography. The methods are sensitive enough to detect single base pair differences between probe and sample for many sequence contexts, and can readily detect multiple mismatches resulting from deletions, insertions, or point mutations.

Figure 1:
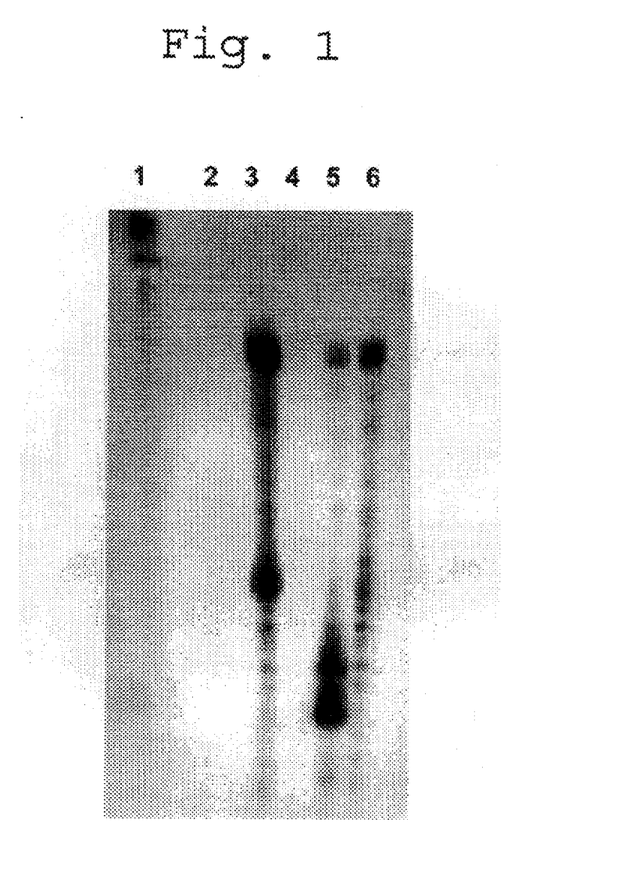
FIG. 1 represents an autoradiograph of a RNase protection assay of the method for detecting mismatches in the genomic DNA-derived PCR products spanning the region, exon 25, intron 25, exon 26, of the ACE gene.

FIG. 1 represents an autoradiograph of a RNase protection assay of the method for detecting mismatches in the genomic DNA-derived PCR products spanning the region, exon 25, intron 25, exon 26, of the ACE gene. The following describes the result shown in FIG. 1. In Lane 1, a free probe is shown. A free probe digested with RNase is represented in Lane 2. Lane 3 shows ACE DNA from an I/I individual. In contrast, Lane 4 shows DNA from an I/I individual lacking ACE. This is confirmed by the genomic DNA-derived PCR products represented by Lane 4 being sequenced and found not to be ACE. Note that no DNA in Lane 4 is protected by the antisense RNA probe. Lane 5 represents DNA from a D/D individual with a 5 base pair insertion near the splice acceptor site which results in smaller protected fragments due to probe/sample mismatch.

Note that some full length (287 base pair) DNA is protected, suggesting that the individual is heterozygous for the insertion. In Lane 6 is shown DNA from a D/D individual without mutations based on genomic DNA sequence. The full length (287 base pair) fragment is protected.

The present invention can be used to screen for mutations in other regions of the ACE cDNA besides the above 287 base pair region. A full length ACE cDNA cloned from an I/I genotype (see Example 1) is used as an antisense RNA probe to detect mismatches in other parts of the coding region. The full length cDNA is divided into 500-1000 base pair segments using convenient restriction enzymes. Each fragment is cloned into a transcription competent vector. Antisense probes transcribed from each fragment are hybridized with 5-10 μg of total RNA extracted from left ventricles of explanted hearts. The initial screening involves a search for coding region mutations only, hence use of total RNA, as the ACE gene is quite large (21000 base pair) (Hubert et al., *J. Biol. Chem.* 266: 15377-15383 (1991)), but the mature mRNA is only 4200 base pair. Mismatches between the probe and tissue RNA results in smaller than expected protected fragments after separation by denaturing gel electrophoresis. If other mutations or clusters of mutations are found, appropriate probes and primers are designed so that PCR-amplified genomic DNA from a larger number of individuals can be screened by the present invention for the mutation(s) to determine mutation frequency.

In detecting the location, i.e., the distance from the end of a labeled probe fragment, of small deletions, insertions, or point mutations in an angiotensin-converting enzyme gene of a human patient predisposing the patient to a cardiovascular disease, a RNase protection assay comprises:

(a) determining an angiotensin-converting enzyme genomic DNA sequence from the patient;

(b) hybridizing the angiotensin-converting enzyme genomic DNA sequence from the patient with a detectable probe specific for a sequence region of the angiotensin-converting enzyme gene from a person with no mutations in the region; and (c) detecting mismatches between the genomic DNA sequence and the probe, wherein mismatches are an indication of the location of small deletions, insertions, or point mutations in the angiotensin-converting enzyme gene of the patient.

In detecting the location, i.e., the distance from the end of a labeled probe fragment, of small deletions, insertions, or point mutations in an angiotensin-converting enzyme gene of a human patient predisposing the patient to a cardiovascular disease, another RNase protection assay comprises:

(a) determining an angiotensin-converting enzyme genomic DNA sequence from the patient;

(b) amplifying a sequence region of the angiotensin-converting enzyme gene from the patient;

(c) hybridizing the amplification products from the patient with a detectable probe specific for a sequence region of the angiotensin-converting enzyme gene from a person with no mutations in the region; and (d) detecting mismatches between the amplification products and the probe, wherein mismatches are an indication of the location of small deletions, insertions, or point mutations in the angiotensin-converting enzyme gene of the patient.

In detecting mutations in an angiotensin-converting enzyme gene of a human patient predisposing the patient to a cardiovascular disease, a single strand conformation polymorphism method comprises:

(a) determining an angiotensin-converting enzyme genomic DNA sequence from the patient;

(b) treating the genomic DNA sequence under denaturing conditions to obtain single-stranded DNA;

(c) hybridizing the single-stranded DNA so obtained with a detectable probe specific for the sequence region of the angiotensin-converting enzyme gene of step (b) from a person with no mutations in the region; and (d) detecting mismatches between the single-stranded DNA and the probe, wherein mismatches are an indication of mutations in the angiotensin-converting enzyme gene of the patient.

In detecting mutations in an angiotensin-converting enzyme gene of a human patient predisposing the patient to a cardiovascular disease, another single strand conformation polymorphism method comprises:

(a) determining an angiotensin-converting enzyme genomic DNA sequence from the patient;

(b) amplifying a sequence region of the angiotensin-converting enzyme gene from the patient;

(c) treating the amplification products under denaturing conditions to obtain single-stranded DNA;

(d) hybridizing the single-stranded DNA so obtained with a detectable probe specific for the sequence region of the angiotensin-converting enzyme gene of step (b) from a person with no mutations in the region; and (e) detecting mismatches between the single-stranded DNA and the probe, wherein mismatches are an indication of mutations in the angiotensin-converting enzyme gene of the patient.

One skilled in the art will readily recognize that a variety of labeled markers can be used with the antisense RNA probe. These markers can be radioactive, fluorescent or enzymatic. The probe may be generated by direct oligo-nucleotide synthesis, for example, using an Applied Biosystems (Foster City, Calif.) DNA synthesizer (model 380b). The probe may be directly labeled with any detectable label known in the art, including radioactive nuclides such as $^{32}P$, $^{3}H$ and $^{35}S$, fluorescent markers such as fluorescein, Texas Red, AMCA blue, lucifer yellow, rhodamine, and the like, or with any cyanin dye which is detectable with visible light. The probe may be labeled using methods such as PCR, random priming, end labelling, nick translation or the like. The probe may also be directly labeled by incorporating nucleotides with an activated linker arm attached, to which a fluorescent market may be added. Alternatively, the probe may also be indirectly labeled by incorporating a nucleotide covalently linked to a hapten or other molecule such as biotin or digoxygenin, and performing a sandwich hybridization with a labeled antibody directed to that hapten or other molecule, or in the case of biotin, with avidin conjugated to a detectable label. Antibodies may be conjugated with a fluorescent marker, or with an enzymatic marker such as alkaline phosphatase or horseradish peroxidase to render them detectable.

Preferred methods for labeling the probe are by random priming, end labelling, PCR and nick translation, but nick translation is preferable. Labeling is conducted in the presence of T7 phage polymerase, three unlabeled nucleotides, and a fourth nucleotide which is either directly labeled, contains a linker arm for attaching a label, or is attached to a hapten or other molecule to which a labeled binding molecule may bind. Suitable direct labels include radioactive nuclides such as $^{32}P$, $^{3}H$ and 35S, fluorescent markers such as fluorescein, Texas Red, AMCA blue, lucifer yellow, rhodamine, and the like, or cyanin dyes which are detectable with visible light. Fluorescent markers may alternatively be attached to nucleotides with activated linker arms which have been incorporated into the probe. The probe may also be indirectly labeled, by incorporating a nucleotide covalently linked to a hapten or other molecule such as biotin or digoxygenin, and performing a sandwich hybridization with a labeled antibody directed to that hapten or other molecule, or in the case of biotin, with avidin conjugated to a detectable label. Antibodies and avidin may be conjugated with a fluorescent marker, or with an enzymatic marker such as alkaline phosphatase or horseradish peroxidase to render them detectable. Conjugated avidin and antibodies are commercially available from companies such as Vector Laboratories (Burlingame, Calif.) and Boehringer Mannheim (Indianapolis, Ind.).

The enzyme can be detected through a colorimetric reaction by providing a substrate and/or a catalyst for the enzyme. In the presence of various catalysts, different colors are produced by the reaction, and these colors can be visualized to separately detect multiple probes. Any substrate and catalyst known in the art may be used. Preferred catalysts for alkaline phosphatase include 5-bromo-4-chloro-3-indolylphosphate (BCIP), nitro blue tetrazolium (NBT) and diaminobenzoate (DAB). Preferred catalysts for horseradish peroxidase include orthophenylenediamine (OPD) and 2,2'-azinobis (3-ethylbenzthiazolinesulfonic acid) (ABTS).

The following examples are presented to illustrate the present invention and to assist one of ordinary skill in making and using the same. The examples are not intended in any way to otherwise limit the scope of the invention.

EXAMPLE 1

Cloning Of Full Length ACE cDNA

Total RNA extracted from left ventricles of hearts of known ACE geneotype without mutations in the junctions between intron 25 and exons 25 and 26 are transcribed into DNA using an RNA-dependent DNA polymerase (Superscript II, Gibco-BRL). The full length cDNA is cloned in two fragments by PCR amplification using nested oligonucleotide primers spanning a unique restriction site. Two rounds of PCR, using nested primers for each fragment, are employed to ensure specificity. The two PCR products are digested with the restriction enzyme to generate compatible ends, then ligated. A final round of PCR amplification using the most 5' and the most 3' primers is conducted. The resulting PCR product, which is the full length cDNA, is gel purified and cloned into the vector pCR II (Invitrogen). The enzyme Deep Vent (New England Biolabs, Beverly, Mass.) is used for PCR amplification as it is more stable than Taq polymerase, has a lower error rate, and is more efficient at extending long templates.

An alternate strategy to clone the full length cDNA is to screen a human heart cDNA library in the expression vector pcDNAI (Invitrogen). Expression in mammalian cells is driven by the CMV promoter which is 5' to the multicloning site. In addition, the vector contains the SV40 intron and polyadenylation signal to ensure proper processing of the mRNA.

To test whether ACE cDNA is represented, the library was aliquoted into four fractions, and each aliquot is screened by PCR amplification using nested outer and inner oligonucleotide primer sets spanning nucleotides 74-446. The sequences of the outer and inner primer sets are given below.

Oligonucleotide primer sequence:
outer primers

5' primer: d(GCTGCCGCTGCTGTTGCTGC) (SEQ ID NO: 1)
3' primer: d(AGGCCCCCGTGTCTGTGAAG) (SEQ ID NO: 2)

inner primers

5' primer: d(CAACTGGACGCCGAACTC) (SEQ ID NO: 3)
3' primer: d(GGGCGATGCCCAGGAAGA) (SEQ ID NO: 4)

Figure 2:
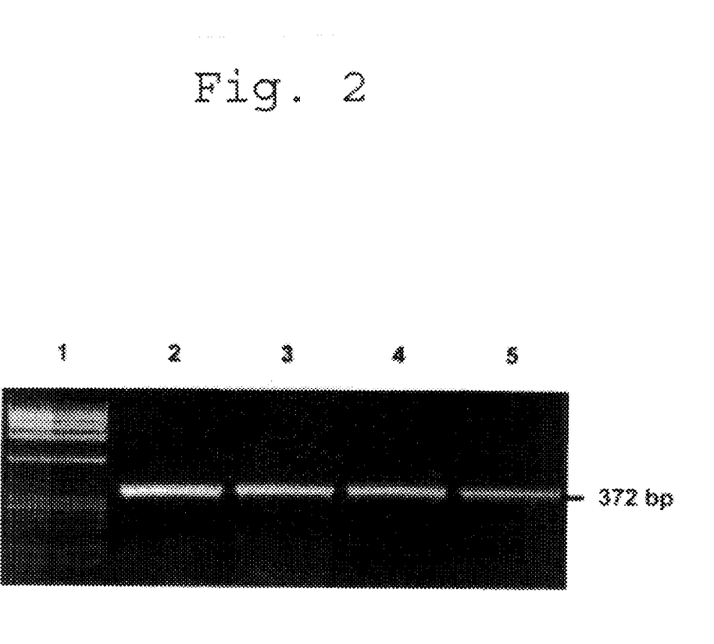
FIG. 2 represents an agarose gel electrophoresis of PCR products derived from amplification of heart cDNA library aliquots.

As shown in FIG. 2, positive aliquots are identified. This indicates that the ACE mRNA is relatively abundant, and that all library aliquots contain full length ACE cDNAs. The positive aliquots are plated on tetracycline/ampicillin agar and colonies screened by hybridization with a 374 base pair ACE cDNA probe spanning nucleotides 74–446. DNA from colonies which hybridize to the probe are rescreened by PCR amplification of plasmid DNA. The size of the inserts are determined by restriction digest using sites flanking the inserts, and full length clones are sequenced to verify they are ACE. The region of the cDNA containing exons 25 and 26 are amplified by PCR using primers described above to test for the presence of 'intron' 25.

The full length ACE cDNA PCR products derived from reverse transcription (RT)-PCR from human heart first is cloned directly into the vector pCRII (Invitrogen). Clones are exercised from pCRII by digestion with EcoRI, as the ACE cDNA does not contain the recognition sequence for the restriction enzyme EcoRI. Then they are recloned into the EcoRI site in the mammalian expression vector pSG5 (Stratagene, La Jolla, Calif.). This vector contains the early SV40 promoter, the rabbit β-globin intron II to facilitate splicing, and a polyadenylation signal to ensure high levels of expression of the cDNA of interest. ACE cDNA clones derived from the heart cDNA library are already in the expression vector pcDNAI (Invitrogen) described above.

ACE expression is tested in transiently transfected COS and CHO cells by assessing ACE enzyme activity and binding of a labeled ACE inhibitor. As either the SV40 or CMV promoter may be less active in some cell lines or with some constructs, other mammalian expression vectors are used if the construct in pSG5 or pcDNAI do not yield high levels of ACE activity.

EXAMPLE 2

Rapid Method For Identifying ACE Mutations By RNase Protection

Assay

The ACE genotype is determined by standard protocol (Marcadet et al., Standardized Southern blot workshop technique, In: Dupont B. (ed) Histocompability Testing, Vol. 1, pp. 553–560, Springer, N.Y. (1986)). D/D and I/D individuals are examined for presence of actual mutations in the following manner. After cloning ACE genomic DNA is digested with restriction enzymes that cleave outside the the 287 base pair region of the ACE gene which spans 134 base pairs of the 3' region of exon 25 and the 5' region of exon 26 and the entire 153 base pairs of intron 25.

The resulting ACE genomic DNA fragments are hybridized in solution with an antisense radiolabeled RNA probe. The antisense radiolabeled RNA probe is prepared in vitro by transcribing cloned DNA, from the region of the ACE gene described above of an I/I individual with no mutations, in the presence of ribonucleotides (ATP, GTP, CTP, and α-$^{32}$P-UTP) and T7 phage polymerase. The lack of mutations in the RNA probe is verified by sequencing. In addition to a radioactive nucleotide, the RNA probe may be labeled with a chemically tagged non-radioactive nucleotide capable of generating a color or photons. The hybridization solution consists of 1 μl ACE genomic DNA fragment (approx. 500 ng) and 100,000 to 300,000 cpm antisense RNA probe in 20 μl hybridization buffer (80% formamide, 40 mM PIPES (pH 6.4) 0.4M NaCl, and 1 mM EDTA). The DNA and RNA probe are denatured at 90° C. for 10 minute. Then the DNA and RNA probe are allowed to anneal at 44° C. for 16–18 hours.

The unhybridized RNA is digested with RNase solution under the following conditions. After hybridization, 350 μl of RNAse solution (RNase A and RNase T1 at 40 μg/ml in 10 mM Tris-HCl (pH 7.5), 1 mM EDTA, 200 mM NaCl, 100 mM LiCl) are added to the hybridization solution and incubated at 25° C. for 30 minutes. The protected DNA fragments are precipitated by addition of 400 μl isopropanol and 40 μl 8M ammonium acetate. The above hybridization and digestion follow a standard protocol (Myers et al., Science 238:1242–1246 (1985)). The protected DNA fragments are resolved by denaturing gel electrophoresis (8% acrylamide, 8M urea gel, 2000V for 3–4 hours) and visualized by autoradiography. The RNase protection assay can determine the relative type of mutation (point mutation versus insertion/deletion) and the relative location of the mutation (distance from end of labeled probe fragment). Because the method does not require prior knowledge of the nature/location of mutations, RNase protection assay can be used to scan sequences for new mutations.

EXAMPLE 3

Rapid Method For Identifying ACE Mutations By Linked Enzymatic

Amplification-RNase Protection Assay

The ACE genotype is determined by standard protocol (Marcadet et al., Standardized Southern blot workshop technique, In: Dupont B. (ed) Histocompability Testing, Vol. 1, pp553–560, Springer, N.Y. (1986)). D/D and I/D individuals are examined for presence of actual mutations in the following manner. Polymerase chain reaction amplification of the region containing the mutations requires utilization of nested oligonucleotide primers to confer specificity of amplification. The outer primers amplify the region of the ACE gene spanning nucleotides 3646–3841 of the cDNA (numbered according to the ACE sequence published by Soubrier et al., Proc. Nat. Acad. Sci. USA 85:9386–9390 (1988)). Polymerase chain reaction amplification of genomic DNA with the outer primer set results in a 348 base pair product (195 base pairs of the 3' region of exon 25 and the 5' region of exon 26 and the entire 153 base pairs of intron 25). PCR products resulting from amplification with the outer primers are diluted 1:100, and reamplified with inner primers, resulting in PCR products spanning nucleotides 3694–3810 of the ACE cDNA. Amplification of genomic DNA using the inner primer set results in a 287 base pair product (134 base pairs of the 3' region of exon 25 and the 5' region of exon 26 and the entire 153 base pairs of intron 25). The sequences of the outer and inner oligonucleotide primer sets are given below.

Oligonucleotide primer sequence:
outer primers

5' primer: d(AACGAGCTGCATGGGGAGAA) (SEQ ID NO: 5)
3' primer: d(GTGGCTACCAGCAGGGCGAT) (SEQ ID NO: 6)

inner primers

5' primer: d(CAACTGGACGCCGAACTC) (SEQ ID NO: 7)
3' primer: d(GGGCGATGCCCAGGAAGA) (SEQ ID NO: 8)

The 287 base pair product resulting from amplification with the inner primer set is excised from agarose gels following electrophoresis and the DNA is eluted (Geneclean Bio101). Then the amplification product is ligated into a cloning vector designed for PCR cloning (TA cloning vector, Invitrogen). Inserts are sequenced from both promoters in the vector to ensure that the sequence of the entire insert is obtained.

The amplification product is hybridized in solution with an antisense radiolabeled RNA probe. The antisense radiolabeled RNA probe is prepared in vitro by transcribing cloned DNA, from the region of the ACE gene described above of an I/I individual with no mutations, in the presence of ribonucleotides (ATP, GTP, CTP, and $\alpha$-$^{32}$P-UTP) and T7 phage polymerase. The lack of mutations in the RNA probe is verified by sequencing. In addition to a radioactive nucleotide, the RNA probe may be labeled with a chemically tagged non-radioactive nucleotide capable of generating a color or photons. The hybridization solution consists of 1 µl amplification product (approx. 500 ng) and 100,000 to 300,000 cpm antisense RNA probe in 20 µl hybridization buffer (80% formamide, 40 mM PIPES (pH 6.4) 0.4M NaCl, and 1 mM EDTA). The DNA and RNA probe are denatured at 90° C. for 10 minute. Then the DNA and RNA probe are allowed to anneal at 44° C. for 16–18 hours.

The unhybridized RNA is digested with RNase solution under the following conditions. After hybridization, 350 µl of RNase solution (RNase A and RNase T1 at 40 µg/ml in 10 mM Tris-HCl (pH 7.5), 1 mM EDTA, 200 mM NaCl, 100 mM LiCl) are added to the hybridization solution and incubated at 25° C. for 30 minutes. The protected DNA fragments are precipitated by addition of 400 µl isopropanol and 40 µl 8M ammonium acetate. The above hybridization and digestion follow a standard protocol (Myers et al., *Science* 238:1242–1246 (1985)). The protected DNA fragments are resolved by denaturing gel electrophoresis (8% acrylamide, 8M urea gel, 2000V for 3–4 hours) and visualized by autoradiography.

EXAMPLE 4

Single Strand Conformation Polymorphism

Single strand conformation polymorphism (SSCP) is a method for mutational analysis which relies on sequence-specific changes in single-stranded DNA conformation in an electric field (Orita et al., *Proc. Nat. Acad. Sci. USA* 86: 2766–2770 (1989)). Genomic DNA or PCR products are denatured to single-stranded DNA (ssDNA) in buffer containing 98% formamide, 2% glycerol, and the tracking dyes, bromophenol blue and xylene cyanol. The ssDNA is resolved by non-denaturing gel electrophoresis. Under the appropriate conditions, the electrophoretic mobility of ssDNA is a function, not only of fragment length and base pair composition (molecular weight), but also a function of its three dimensional structure or conformation. In SSCP, the complementary strands of DNA migrate at slightly different rates due to the different base pair compositions and different conformations of the strands. Nucleotide changes as small as a single base pair transition are evident as changes in relative mobility of the altered ssDNA. Thus, mutant alleles will migrate differently from analogous wild-type alleles. If DNA fragments from individuals heterozygous for mutations within the fragments are analyzed by SSCP, three or four bands should be detected compared with two bands in DNA fragments from individuals bearing no mutations. DNA fragments from individuals homozygous for the same mutations should yield two bands, but of different mobility from wild-type, on SSCP analysis.

Bands may be detected by incorporating $\alpha$-$^{32}$P-dCTP, or non-radioactive dCTP conjugates such as biotin-dCTP or digoxigenin-dCTP into the enzymatic amplification reaction. Following electrophoresis, appropriate developing reagents may be applied and the gel exposed to film. The polyacrylamide gel may also be directly silver stained after electrophoresis of samples to visualize the bands. As enzymatic amplification greatly increases the concentration of DNA in small sample volumes, silver staining is sensitive enough to be used for SSCP analysis.

This method identifies the presence of mutations within discrete fragments of DNA (100–500 bp ideal length) and suggests whether the source is heterozygous or homozygous for the mutations. SSCP cannot determine the nature of the mutations (point, insertion or deletion), the sequence of the mutations or the location of the mutations within the fragment. Because the method does not require prior knowledge of the nature/location of mutations, SSCP can be used to scan sequences for new mutations.

EXAMPLE 5

Allele Specific Oligonucleotide Hybridization

Allele specific oligonucleotide hybridization (ASO) can be used to determine single base pair differences in genomic DNA or PCR products based on stringency of hybridization and wash conditions (Saiki et al., *Nature* 324:163–167 (1986)). PCR products are immobilized on solid substrate such as nylon or nitrocellulose membranes, and hybridized sequentially with labeled single-stranded oligonucleotide probes corresponding to the wild-type and mutant alleles. Hybridization and wash conditions must be optimized for the wild-type and the mutant probes so that only complementary probe sequences will bind stably under the given conditions. This method determines whether an individual is homozygous for the wild-type allele, heterozygous or homozygous for the mutant allele. ASO hybridization requires prior knowledge of the exact sequence of mutations as complementary oligonucleotide probes must be synthesized. This method can be used to detect the A to G transition near the splice acceptor site in intron 25. The method requires synthesis of mutation-specific oligonucleotide probes for each mutation identified.

EXAMPLE 6

Amplification Refractory Mutation System

The amplification refractory mutation system (ARMS) is based on the inability of Taq Polymerase to synthesize a new DNA strand in the polymerase chain reaction if the 3' nucleotide of the oligonucleotide primer does not match the template DNA (Newton et al., *Nucl. Acids Res.* 17:2503–2516 (1989)). Thus, PCR primers can be designed such that the 3' nucleotide of either primer is the normal or altered nucleotide. Each genomic DNA sample is amplified in two separate reactions, one using the wild-type or normal primer and one using the mutant primer. PCR conditions are optimized such that the wild-type primer amplifies only the normal allele and the mutant primer amplifies only the mutant allele. The ARMS method can be used to identify point mutations in the region of the ACE gene spanning exon 25-intron 25-exon 26. Specific primers containing each sequence variant can be designed such that the variant (either point mutation, insertion or deletion) is at the 3' end of the primer.

The frequency of the D/D genotype is approximately 28–30% in the general population, but is lower (24%) in individuals with few risk factors for cardiovascular disease. The frequency of the D/D genotype is increased in individuals who have had myocardial infarctions, but who do not have any of the classic risk factors (32%). The D/D genotype frequency is also increased in individuals with end stage heart failure (36–39%). The polymorphic markers in intron 16 are genetically close to changes in the ACE gene locus which are associated with heart disease, but are not themselves the true variants. The invention described herein provides a direct determination of true genetic variants responsible for cardiovascular disease. The mutations identified in intron 25, which is retained in the mature ACE mRNA in the heart, are allelic with the D allele. As these mutations affect the expressed ACE protein, they are much more likely to correlate with alterations in ACE function which may contribute to disease. Direct screening for the mutations provides an improved way to predict the risk for heart disease contributed by ACE. The screening method of the invention is rapid and can be performed using genomic DNA extracted from dried blood (finger stick), buccal swab, or hair follicle. No biopsies are necessary.

Another use of the invention is in genotype-based clinical trials of ACE inhibitors. In these trials individuals of known ACE genotype are tested to determine whether inhibitor therapy is more beneficial in individuals with mutations. The results of these trials will show the efficacy of ACE inhibitor therapy for these individuals. Such therapy includes preventing recurrence of myocardial infarction and progression of left ventricular function, and improvement of long term survival in individuals with congestive heart failure. Long term trials of ACE inhibitor therapy may be conducted in families with strong histories of heart disease to examine whether prophylactic inhibition of ACE activity abolishes or delays myocardial infarctions.

As will be apparent to those skilled in the art in which the invention is addressed, the present invention may be embodied in forms other than those specifically disclosed above without departing from the spirit or essential characteristics of the invention. The particular embodiments of the present invention described above, are, therefore, to be considered in all respects as illustrative and not restrictive. The scope of the present invention is as set forth in the appended claims rather than being limited to the examples contained in the foregoing description.

---

What is claimed is:

1. A method of detecting small deletions, insertions, or point mutations in an angiotensin-converting enzyme gene of a human patient which is used to assess the patient's risk for developing cardiovascular disease, comprising the steps of:
   (a) isolating an angiotensin-converting enzyme genomic DNA sequence from the patient, wherein the sequence region of the angiotensin-converting enzyme gene is a base pair region spanning intron 25 using oligonucleotide primers in the 3' region of exon 25 and the 5' region of exon 26;
   (b) hybridizing the angiotensin-converting enzyme genomic DNA sequence from the patient with a detectable probe specific for a sequence region of the angiotensin-converting enzyme gene from a person with no mutations in the region; and
   (c) detecting mismatches between the genomic DNA sequence and the probe, wherein mismatches are an indication of small deletions, insertions, or point mutations in the angiotensin-converting enzyme gene of the patient.

2. A method of detecting small deletions, insertions, or point mutations in an angiotensin-converting enzyme gene of a human patient which is used to assess the patient's risk for developing cardiovascular disease, comprising the steps of:
   (a) isolating an angiotensin-converting enzyme genomic DNA sequence from the patient, wherein the sequence region of the angiotensin-converting enzyme gene is a base pair region spanning intron 25 using oligonucleotide primers in the 3' region of exon 25 and the 5' region of exon 26;
   (b) amplifying the sequence region of the angiotensin-converting enzyme gene from the patient;
   (c) hybridizing the amplification products from the patient with a detectable probe specific for the sequence region of the angiotensin-converting enzyme gene of step (b) from a person with no mutations in the region; and
   (d) detecting mismatches between the amplification products and the probe, wherein mismatches are an indication of small deletions, insertions, or point mutations in the angiotensin-converting enzyme gene of the patient.

3. A method of detecting mutations in an angiotensin-converting enzyme gene of a human patient which is used to assess the patient's risk for developing cardiovascular disease, comprising the steps of:
   (a) isolating an angiotensin-converting enzyme genomic DNA sequence from the patient, wherein the sequence region of the angiotensin-converting enzyme gene is a base pair region spanning intron 25 using oligonucleotide primers in the 3' region of exon 25 and the 5' region of exon 26;
   (b) treating the genomic DNA sequence under denaturing conditions to obtain single-stranded DNA;
   (c) hybridizing the single-stranded DNA so obtained with a detectable probe specific for a sequence region of the angiotensin-converting enzyme gene from a person with no mutations in the region; and
   (d) detecting mismatches between the single-stranded DNA and the probe, wherein mismatches are an indication of mutations in the angiotensin-converting enzyme gene of the patient.

4. A method of detecting mutations in an angiotensin-converting enzyme gene of a human patient which is used to assess the patient's risk for developing cardiovascular disease, comprising the steps of:
   (a) isolating an angiotensin-converting enzyme genomic DNA sequence from the patient, wherein the sequence region of the angiotensin-converting enzyme gene is a base pair region scanning intron 25 using oligonucleotide primers in the 3' region of exon 25 and the 5' region of exon 26;
   (b) amplifying the sequence region of the angiotensin-converting enzyme gene from the patient;
   (c) treating the amplification products under denaturing conditions to obtain single-stranded DNA;
   (d) hybridizing the single-stranded DNA so obtained with a detectable probe specific for the sequence region of the angiotensin-converting enzyme gene of step (b) from a person with no mutations in the region; and
   (e) detecting mismatches between the single-stranded DNA and the probe, wherein mismatches are an indication of mutations in the angiotensin-converting enzyme gene of the patient.

5. The method according to claim 1, wherein the oligonucleotide primer sequences are d(CAACTGGACGCCGAACTC) for the 5' primer and d(GGGCGATGCCCAGGAAGA) for the 3' primer.

6. The method according to claim 2, wherein the oligonucleotide primer sequences are d(CAACTGGACGCCGAACTC) for the 5' primer and d(GGGCGATGCCCAGGAAGA) for the 3' primer.

7. The method according to claim 3, wherein the oligonucleotide primer sequences are d(CAACTGGACGCCGAACTC) for the 5' primer and d(GGGCGATGCCCAGGAAGA) for the 3' primer.

8. The method according to claim 4, wherein the oligonucleotide primer sequences are d(CAACTGGACGCCGAACTC) for the 5' primer and d(GGGCGATGCCCAGGAAGA) for the 3' primer.

* * * * *